US007496453B2

(12) United States Patent  (10) Patent No.: US 7,496,453 B2
Chau  (45) Date of Patent: Feb. 24, 2009

(54) CLASSIFICATION OF HERBAL MEDICINES USING WAVELET TRANSFORM

(75) Inventor: Foo-Tim Chau, Hong Kong (HK)

(73) Assignee: The Hong Kong Polytechnic University, Kowloon (HK)

( * ) Notice: Subject to any disclaimer, the term of this patent is extended or adjusted under 35 U.S.C. 154(b) by 0 days.

(21) Appl. No.: 11/557,113

(22) Filed: Nov. 7, 2006

(65) Prior Publication Data
US 2008/0109174 A1  May 8, 2008

(51) Int. Cl.
*G06F 19/00* (2006.01)
*G01N 31/00* (2006.01)

(52) U.S. Cl. ............................. 702/32; 702/19; 702/70; 702/189; 382/130; 382/203; 382/261; 73/23.22; 375/240.19

(58) Field of Classification Search .................. 702/19, 702/32, 70, 189, 190; 382/130–131, 203, 382/261; 704/220, 223; 375/240.19; 73/23.22
See application file for complete search history.

(56) References Cited

U.S. PATENT DOCUMENTS

| 5,384,725 | A | * | 1/1995 | Coifman et al. ............. 708/801 |
| 5,561,431 | A | | 10/1996 | Peele et al. |
| 5,610,843 | A | * | 3/1997 | Chou ......................... 702/109 |
| 5,825,936 | A | | 10/1998 | Clarke et al. |
| 5,867,118 | A | | 2/1999 | McCoy et al. |
| 5,987,094 | A | | 11/1999 | Clarke et al. |
| 6,105,015 | A | | 8/2000 | Nguyen et al. |
| 6,154,600 | A | | 11/2000 | Newman et al. |
| 6,496,797 | B1 | | 12/2002 | Redkov et al. |
| 6,567,081 | B1 | | 5/2003 | Li et al. |
| 6,594,391 | B1 | | 7/2003 | Quadranti et al. |
| 6,650,779 | B2 | | 11/2003 | Vachtesvanos et al. |
| 6,728,645 | B1 | | 4/2004 | Kozlov et al. |
| 6,735,342 | B2 | | 5/2004 | Felts et al. |
| 6,801,573 | B2 | | 10/2004 | Zheng |
| 6,829,384 | B2 | | 12/2004 | Schneiderman et al. |
| 6,871,165 | B2 | | 3/2005 | Aggarwal |
| 6,931,269 | B2 | | 8/2005 | Terry |
| 6,950,755 | B2 | | 9/2005 | Stahl |
| 6,957,172 | B2 | | 10/2005 | Wegerich |
| 7,035,467 | B2 | * | 4/2006 | Nicponski .................... 382/224 |

OTHER PUBLICATIONS

Brown et al., 'Bayesian Wavelet Regression on Curves with Application to a Spectroscopic Calibration Problem', 2001, American Statistical Association, pp. 398-408.*

(Continued)

*Primary Examiner*—Edward Raymond
*Assistant Examiner*—Elias Desta
(74) *Attorney, Agent, or Firm*—Evan Law Group LLC

(57) ABSTRACT

An efficient, effective and reliable method for authentication of herbal medicines (HMs) based on a novel wavelet-enhanced automated three-dimensional chromatograms classification system. The method takes advantage of the character of 3D chromatograms which appear as functional curves and the preprocessing power of wavelet transform (WT) to minimize the interferences from noises and baseline drifting of the raw data, and at the same time significantly reduces the data sizes. This compressed data retain the essential features of the original raw data, whereby leading to efficient and reliable method for identifying or authenticating herbal medicines or other chemical mixtures of great complexity.

18 Claims, 10 Drawing Sheets

The three-dimensional plot of the C1 data with interference free.

OTHER PUBLICATIONS

Przelaskowski, 'Performance Evaluation of JPEG2000-LIKE Data Decomposition Schemes in Wavelet CODEC', 2001, IEEE Publication, pp. 788-791.*

Werness et al. 'Experiments with Wavelets for Compression of SAR Data', Jan. 1994, IEEE Publication, vol. 32, No. 1, pp. 197-201.*

Gonzaga et al. , 'Use of Near Infrared Emission Spectroscopy in the study of Supporting materials and stationary phases for liquid chromatography', 2006, Journal of Chromatography, 174-179.*

Vasudevan et al., 'Simultaneous Estimation of phenylpropanolamine HCL guaiphenesin and diphenylpyraline HCL in Syrups by LC', 2000, Pharmaceutical & Biomedical Journal, pp. 25-31.*

WHO, General Guidelines for Methodologies on Research and Evaluation of Traditional Medicines, 2000, 80 pages.

SFDA, Chinese Traditional Patent Medicine, vol. 22 (2000), pp. 671-675 (in Chinese).

Y.Z. Liang, P. Xie, K. Chan, J. Chromatogr B., 812 (2004) 53-70.

D.K.W. Mok, F.T. Chau, "Chemical information of Chinese medicines: A challenge to chemist", Chemo. Intelli. Lab. Syst., 82(2006) 210-217.

J.O. Ramsay, C.J. Dalzell, J. R. Statist. Soc. B., 1991, 53, 539-572.

C.J. Xu, Y.Z. Liang, Y. Li ,Y.P. Du, Analyst, 128 (2003) 75-81.

B. Walczak, D. L Massart, Trends in Anal. Chem., 16(1997) 451-463.

X.G. Shao, A.K.M. Leung, F.T. Chau, Acc. Chem. Res., 36(2003) 276-283.

K. Jetter, U. Depczynski, K. Molt, A. Niemöller, "Principles and Applications of Wavelet Transformation to Chemometrics", Anal. Chim. Acta., 420 (2000) 169-180.

S. Mallat, IEEE Trans. Pattern Anal. Mach. Intell., 11 (1989) 674-693.

* cited by examiner

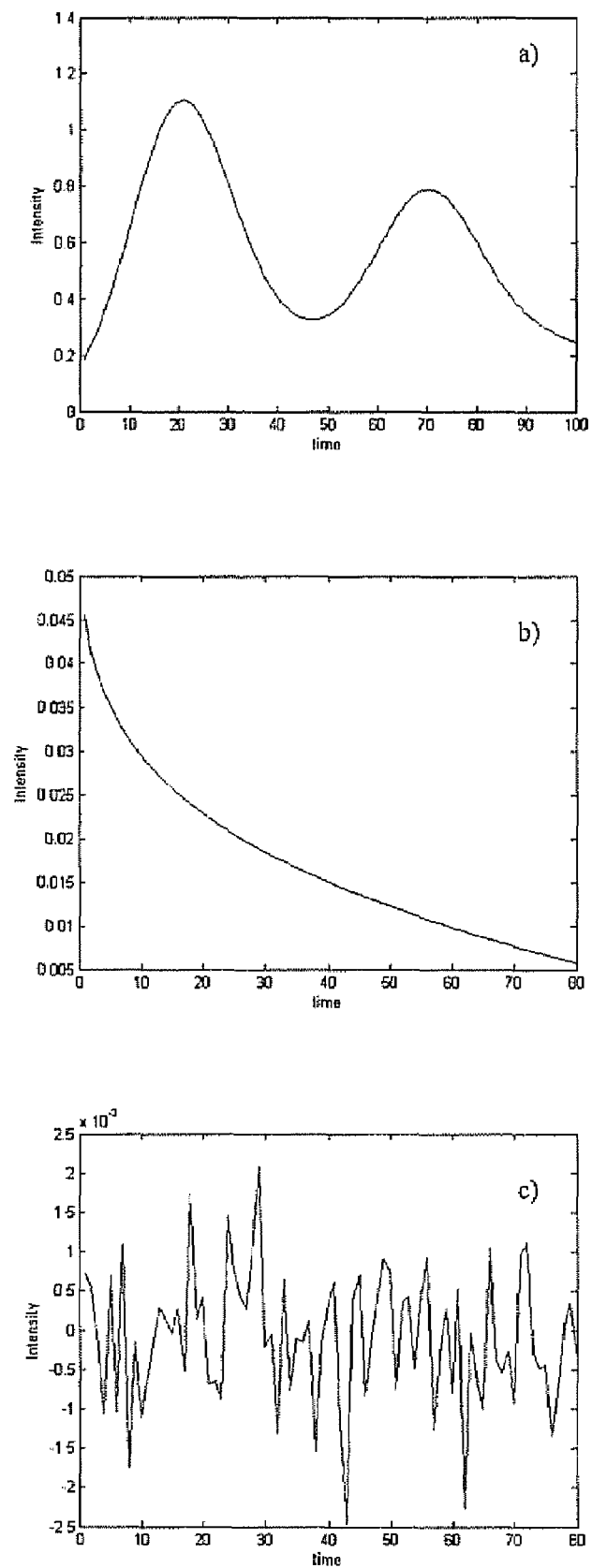
Fig.1 An illustration of a) spectra signal b) baseline line c) noise

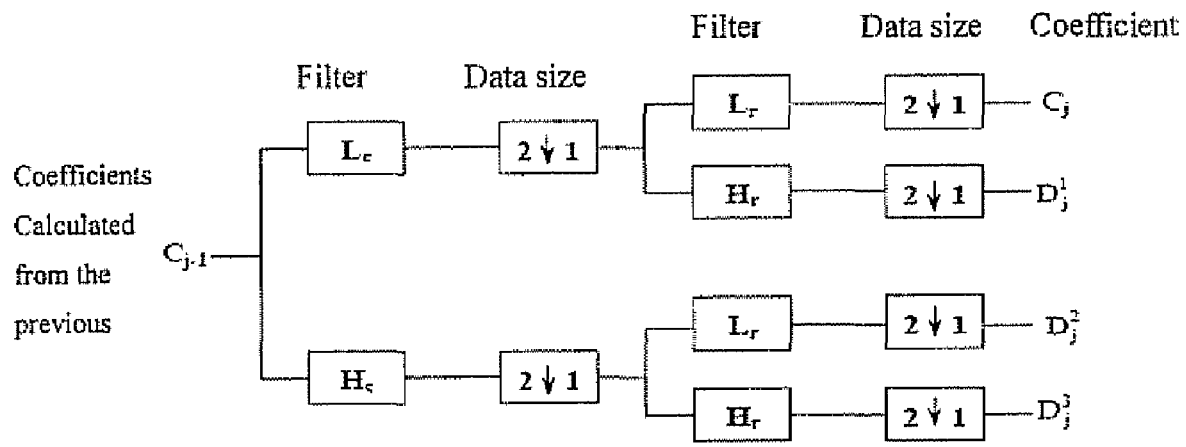
Fig.2. A schematic Diagram for data compression by WT3DC
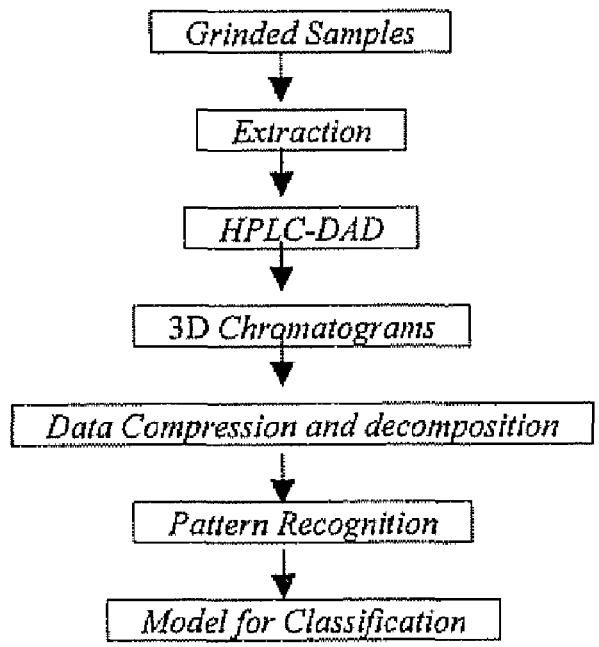
Fig. 3. Flowchart of the WT3DC Technique

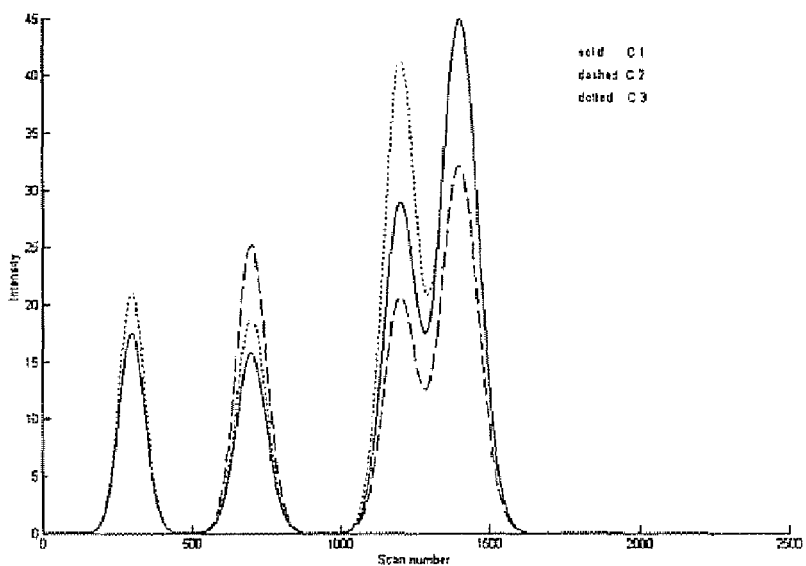
Fig. 4. The three synthetic chromatograms C1 (solid), C2 (dashed), and C3 (dotted) (in 2D form).
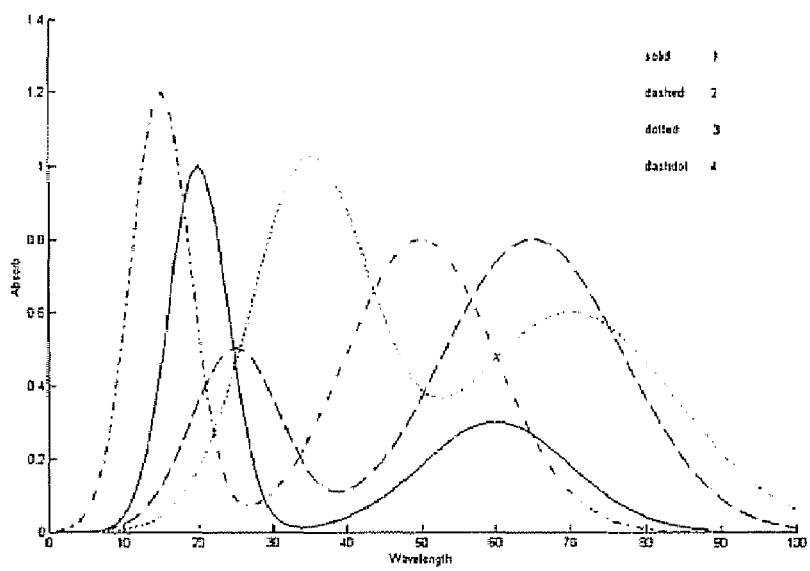
Fig. 5. Synthetic UV spectra of components 1 (solid), 2 (dashed), 3 (dotted), and 4 (dashdot).

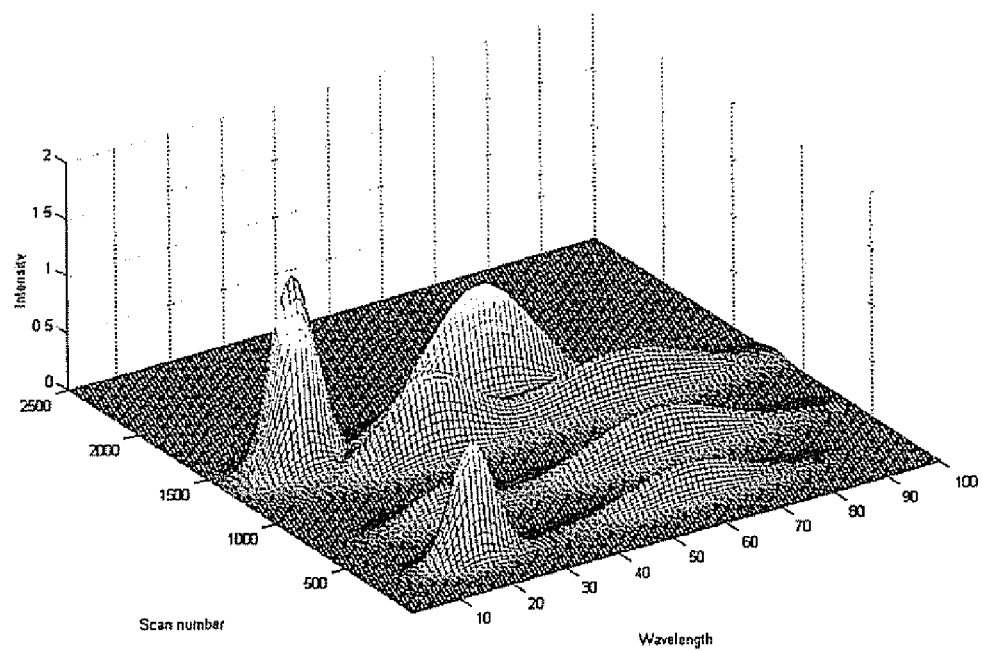
Fig. 6. The three-dimensional plot of the C1 data with interference free.
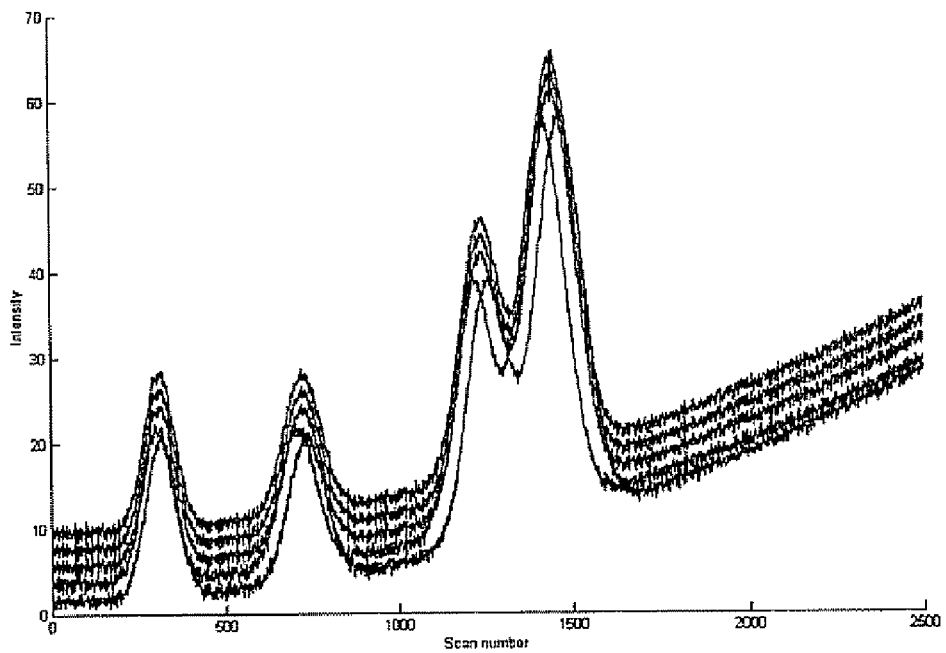
Fig. 7. Five synthetic profiles of chromatogram C1 with noise and baseline drifting (see text for details).

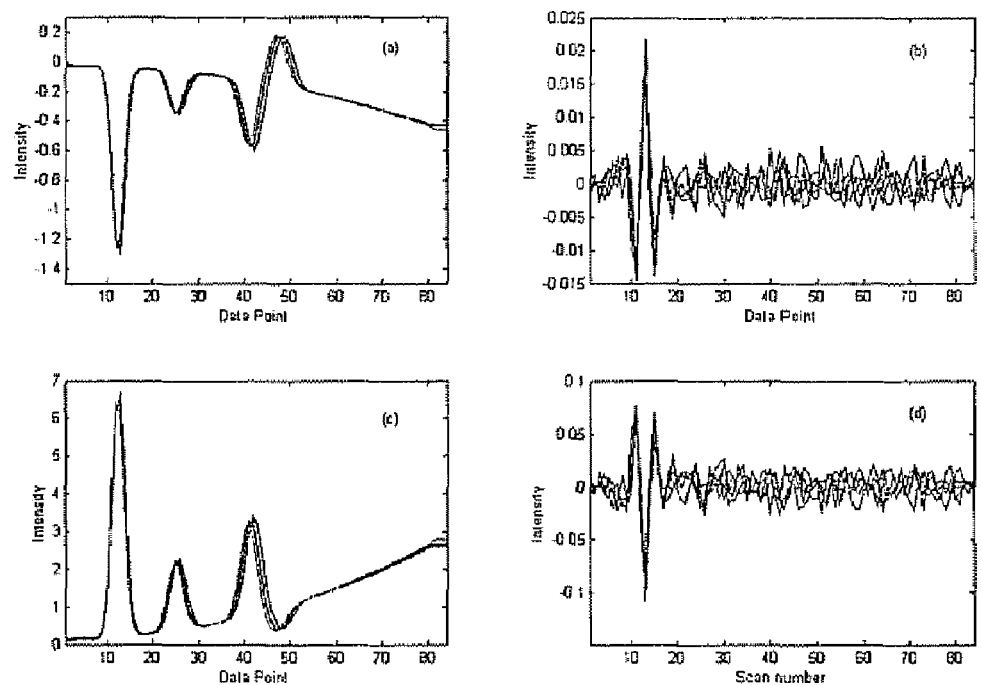
Fig. 8. Plots of the coefficients (a) $C_6$, (b) $D_6^1$, (c) $D_6^2$, and (d) $D_6^3$ obtained by WT treatment on the five synthetic profiles as (Fig. 4) by wavelet Sym4 at scale 6.

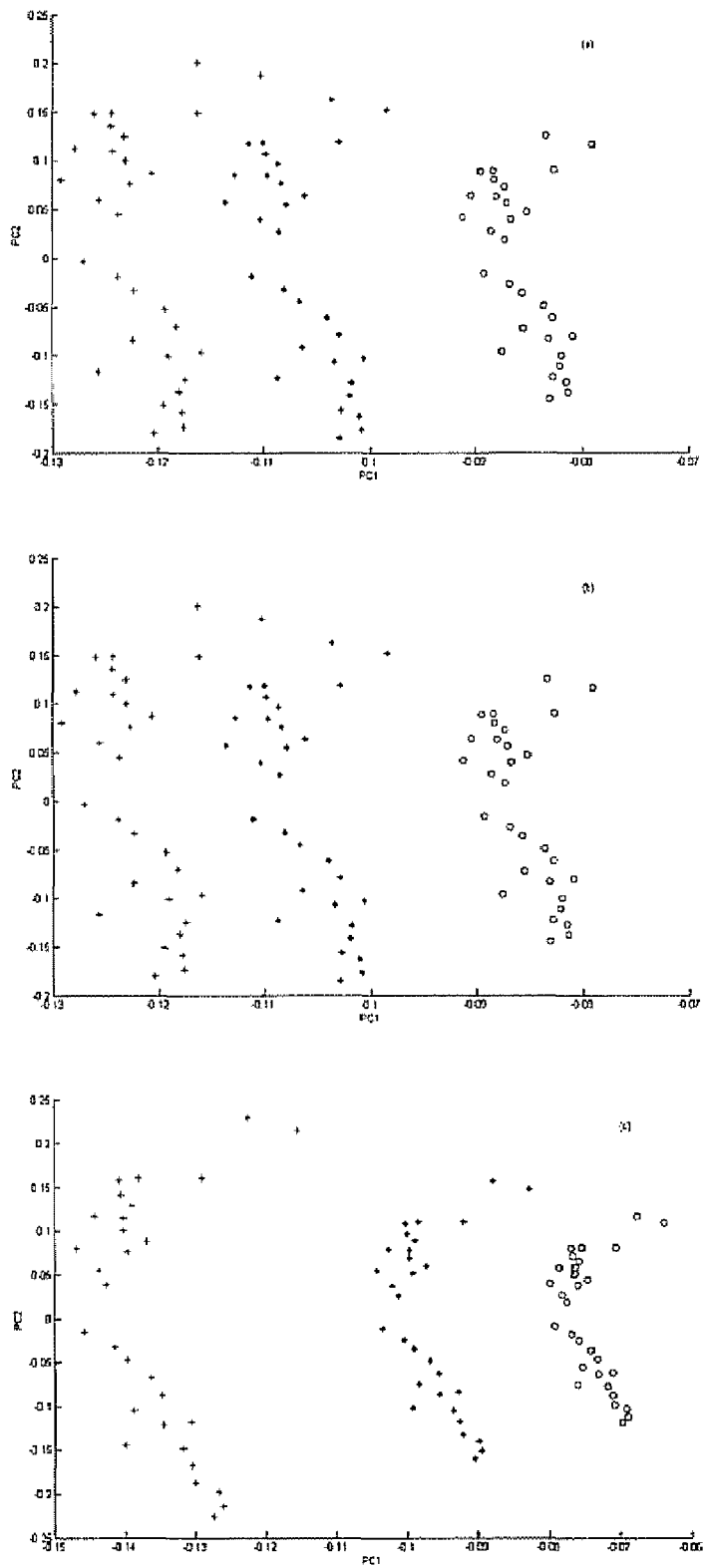
Fig. 9. The PCA plots of the results obtained by using CH2DC (a), WT2DC (b), and WT3DC (c) on treating the C1, C2 and C3 data sets generated with $Fp=10.0\%$, $Nl=0$, and $Bd=0$ (See $GI$ of Table 3).

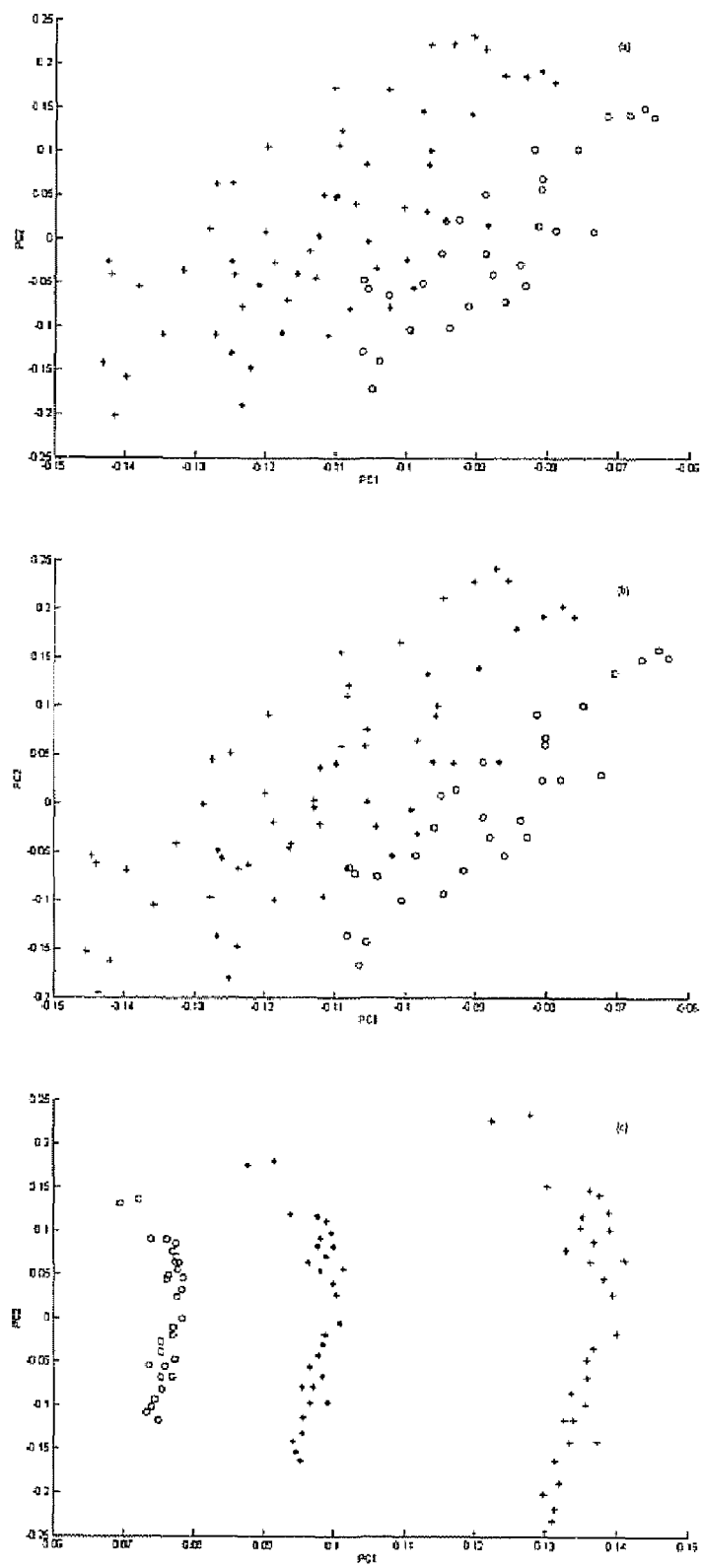
Fig. 10. The PCA plots of the results obtained by using CH2DC (a), WT2DC (b), and WT3DC (c) on treating the C1, C2, and C3 data sets generated with $Fp=6.0\%$, $Nl=6.0\%$, and $Bd=60\%$ (See $G4$ of Table 3).

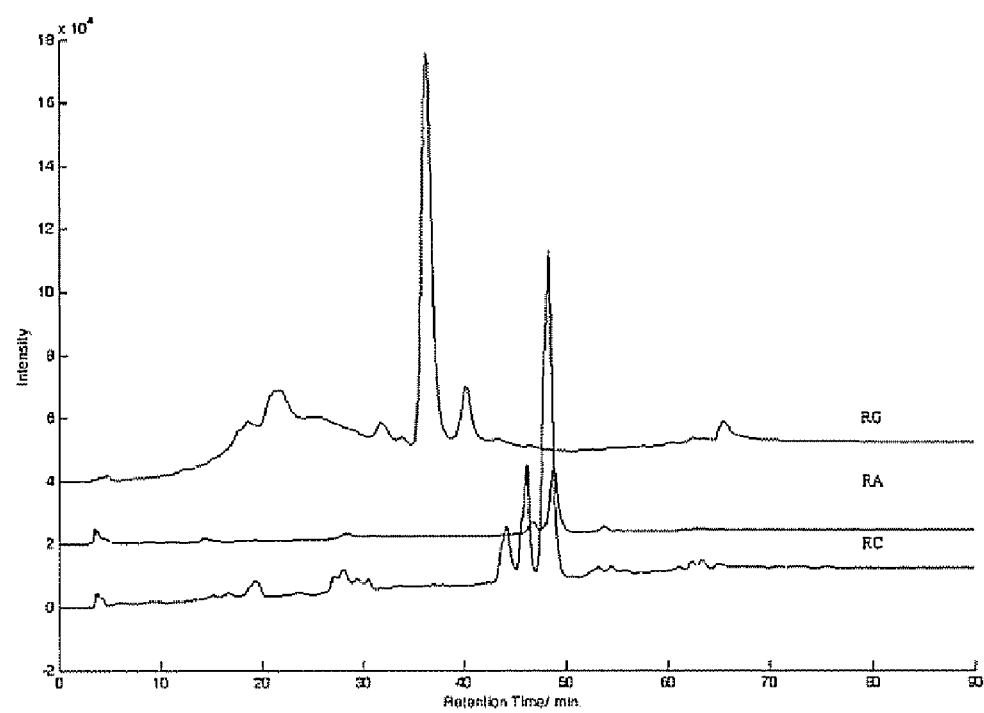
Fig. 11. The pseudo-2D chromatogram of the three Chinese herbs, RA, RC, and RG with their intensities obtained by summing up absorbances at all the wavelengths measured at a given retention time.

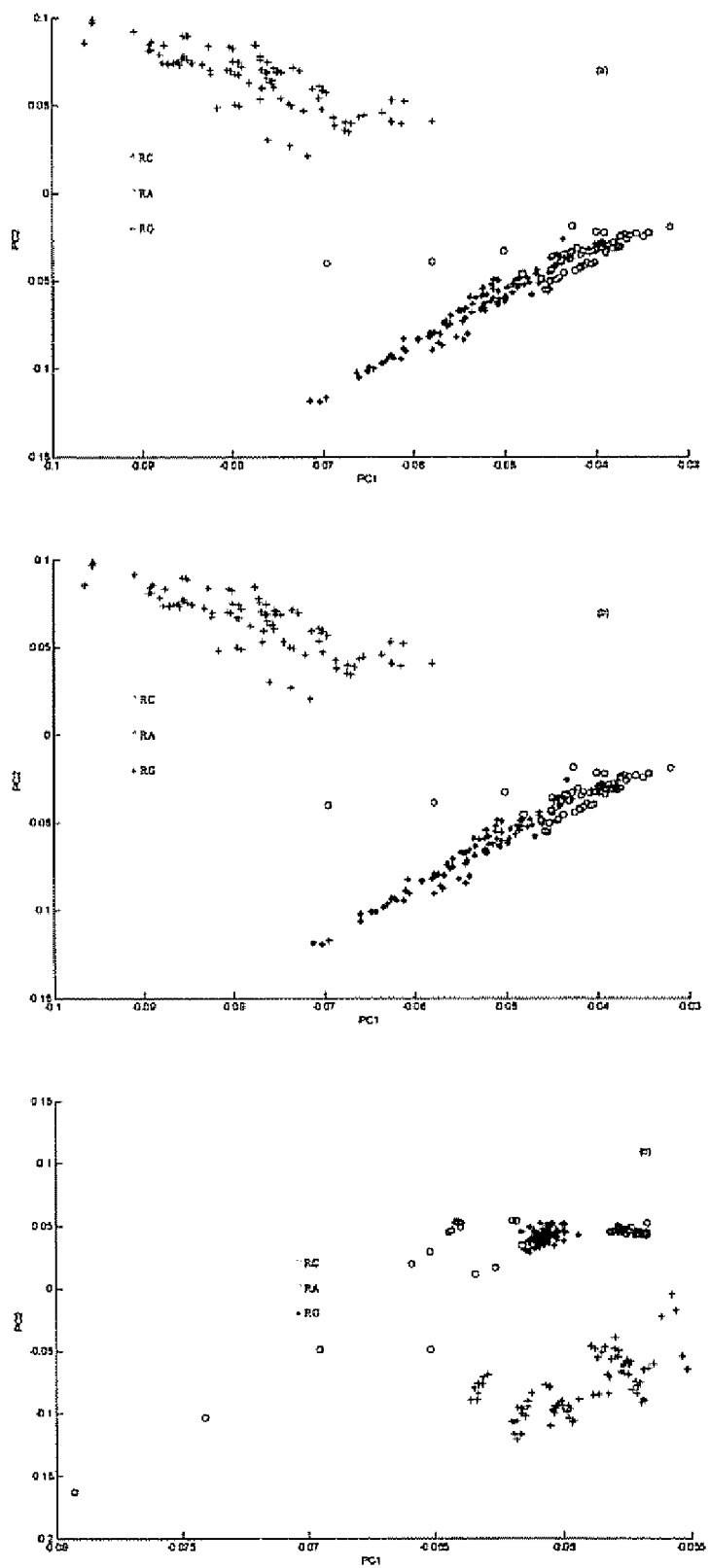
Fig. 12. The two-dimensional PCA plots of the three groups of herbs, RC (*), RG (+) and RA (o), by using results obtained from (a) CH2DC, (b) WT2DC, and (c) WT3DC.

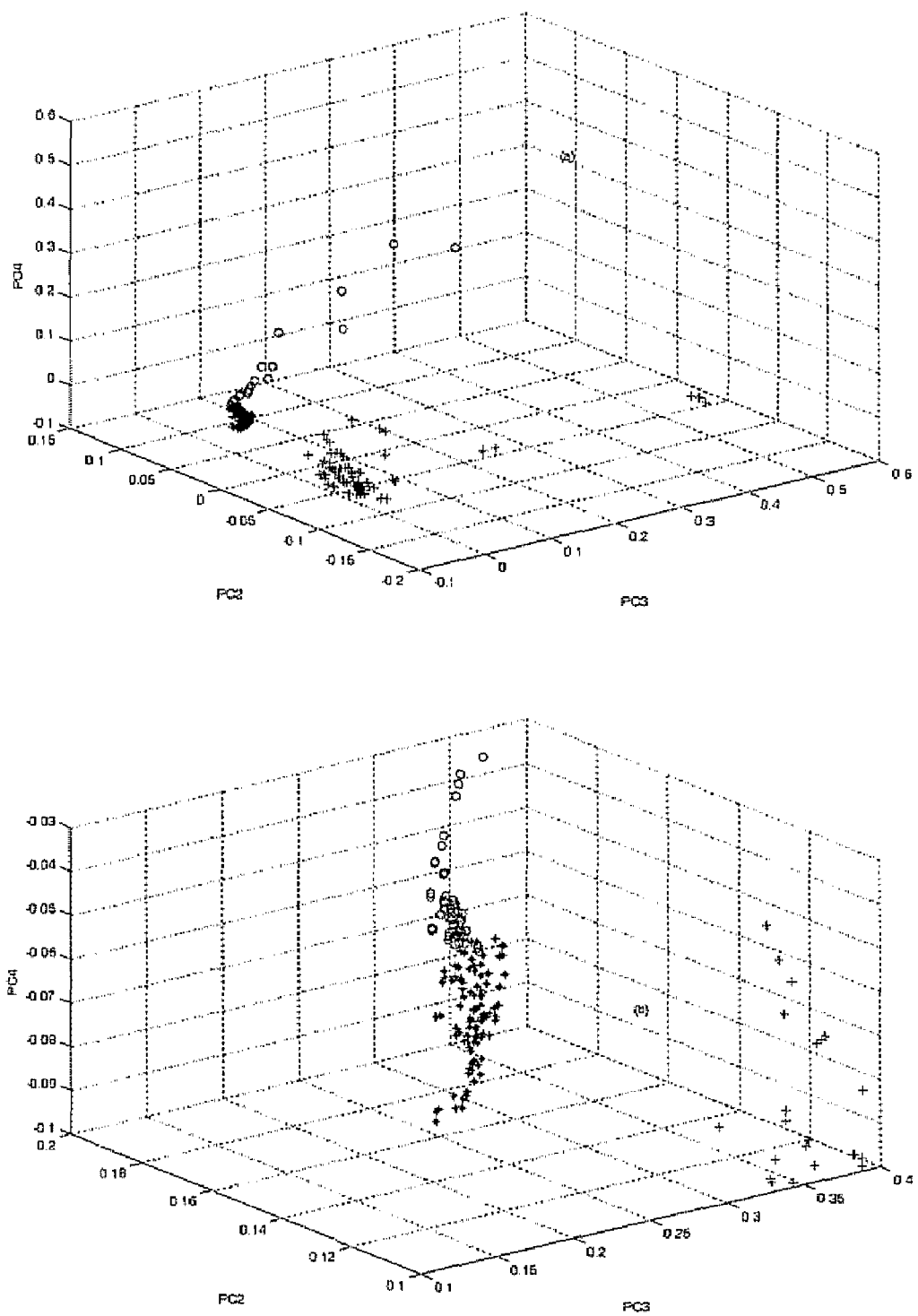
Fig. 13. (a) The three-dimensional PCA plots of the three groups of herbs, RC (*), RG (+) and RA (o), by using results obtained from WT3DC and (b) the enlarged plot.

CLASSIFICATION OF HERBAL MEDICINES USING WAVELET TRANSFORM

FIELD OF THE INVENTION

The present invention relates to pre-processing of raw data set prior to being used for classification. Particularly, it relates to a data processing method based on wavelet transform to extract useful information for subsequent classification and reduce data size, and to its application in classification and authentication of herbal medicines.

BACKGROUND OF THE INVENTION

Herbal Medicines (HMs) have been widely used for disease prevention and treatment over many centuries in Asian areas and, even with advance of modern western medicine, become more and more popular throughout the world. However, due to the fact that in HM herbs there may be hundreds of components for which knowledge is available, it is almost impossible to identify all these substances and to carry out useful quantitative analysis. Therefore, chromatographic fingerprint methods have been highly recommended for quality control purposes by many official authorities [1-4].

When the samples are analyzed by the hyphenated chromatography such as HPLC-DAD (High Performance Liquid Chromatography Diode Array Detector), HPLC-IR (High Performance Liquid Chromatography infrared spectroscopy), Capillary Electrophoresis-Diode Array Detection (CE-DAD), and High Performance Liquid Chromatography Nuclear Magnetic Resonance Spectroscopy (HPLC-NMR), the measured data sets usually can be collected as a two dimensional data matrix, expressed as X (m×n), where the m rows are spectra taken at regular time intervals and the n columns represent chromatograms measured at consecutive wavelengths. The two dimensional data matrix, referred to as three dimensional chromatograms in this application, can reveal qualitative and quantitative information of the samples under study, and it can be utilized to characterize and identify the HM.

However, there are problems that may hamper the use of these three dimensional chromatograms to set up the fingerprint of HM. For example, the HM samples are very complex chemical systems and their data size is usually very large. This means that more storage space is needed and also longer computation time is required in data processing. For instance, 2,862 million data points are obtained for a sample run of 90 minutes by using the instrument Agilent HPLC-DAD 1100. Moreover, baseline drifting and retention time shift are major problems when using these chromatograms for quality control. Therefore, pretreatment of the raw data seems to be an important step in extracting and obtaining useful information [3].

Recently, wavelet transform (WT)[8-11] has been applied in many diverse fields of science, and is now becoming of interest in analytical chemistry. The essence of the WT is that it decomposes a signal into localized contributions labeled by a scale and a position parameter. For the functional data or smooth 3D chromatograms, each of the contributions represents the information of different frequency contained in the original signal. That is to say, the noise, the signal and the drifting baseline are usually considered to be present in the contributions in high, medium, and low frequency band, respectively. Moreover, after WT the total data length and the storage space will be reduced greatly if only the signal information, i.e., the medium band is selected for signal reconstruction after WT treatment. WT treatment results in a set of coefficients. The set of coefficients is much smaller in size yet contains sufficient useful information present in the original data set if an appropriate level of WT treatment is being used.

Conventionally, HM fingerprint analysis (for authentication or quality control) is based on raw data directly obtained from the measuring instrument. The approach of directly using raw data for fingerprint authentication does not make good use of the information-rich measurement data sets. The data sets measured by, for example, HPLC-DAD, are not only univariate or multivariate observations, but also functions observed continuously. In other words, they are smooth curves along the time line. Such special characters of the data, if being handled efficiently, will certainly improve the predictive accuracy [5-7]. There is therefore a need for a better way of performing HM fingerprint analysis.

SUMMARY OF THE INVENTION

It is an object of the present invention to provide a method of pre-treating or pre-process raw data obtained from the measuring instrument in the process of performing fingerprint analysis of herbal medicines to remove irrelevant information and reduce the data size and yet retain useful information for the purpose of classification, authentication and quality control. The irrelevant information includes, noise, baseline shift, etc.

It is a further object of the present invention to provide a method and system for authenticating an herbal medicine by more efficiently using the information-rich three dimensional chromatograms.

These and other objects of the present invention are realized by pre-processing raw data of three dimensional chromatograms based on a Wavelet Transform (WT) technology.

Following the WT treatment according to the present invention, a pre-processing method referred to in the following as WT3DC, the resulting coefficients can be utilized directly for classification, calibration and regression without further reconstruction steps. The performance of the WT3DC method was evaluated through the simulated data with variations in baseline, noise level, retention time shift and peak parameters, and further evaluated by real HPLC-DAD chromatographic data for an HM sample. With the preprocessing power of wavelet transform, the interferences from noise and drifting of the raw data have been largely eliminated. Furthermore, the data size is significantly reduced, but the essential features of the data sets are still retained. Thus, the WT coefficients obtained accordingly to the present invention can facilitate subsequent classification and identification model building.

As a particular embodiment, the present invention provides a method of identifying or authenticating a substance containing a plurality of chemical ingredients, comprising the steps of: (a) obtaining a data set from a sample of a substance with a measuring instrument; (b) transforming said data set using a wavelet with a vanishing moment to yield a set of coefficients at a decomposition scale; and (c) optionally classifying said set of coefficients with a classification method to afford a classification result; preferably, the wavelet is Sym4; the vanishing moment is 4; and decomposition scale is 5 or 6.

As another particular embodiment, the present invention provides a device for identifying or authenticating a substance containing a plurality of chemical ingredients, such as, herbal medicines, which comprises (a) an data interface adapted for connecting with a measuring instrument and receiving a data set from said measuring instruments; and (b) a data compression module capable of performing a wavelet transform on said data set to produce a set of coefficients at a given decomposition scale, said module allowing selection of a wavelet, a vanishing moment, and a decomposition scale for performing said wavelet transform. The device may further comprise a data classification module for performing classification on said set of coefficients and outputting a classification result. The data compression module and data classification module may be implemented in hardware, software or combination of hardware and software. The data interface may be a serial port, parallel port, firewire port, USB port, WiFi connection, bluetooth connection or infrared connection. The device may be a personal computer with both data compression and classification modules being implemented in software. The software implementation of the compression and classification modules can be achieved by persons with ordinary skill related to the pertinent art. Optionally, the classification result may be visually presented on a screen or printout on paper.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

BRIEF DESCRIPTION OF DRAWINGS

FIGS. 1(a), 1(b) and 1(c) are illustrations of the spectra signal, the baseline line, and the noise respectively;

FIG. 2 is a schematic diagram for data compression by the wavelet-enhanced automated three-dimensional chromatograms classification system;

FIG. 3 is a flowchart of the wavelet-enhanced automated three-dimensional chromatograms classification system;

FIG. 4 is the three synthetic chromatograms C1 (solid), C2 (dashed), and C3 (dotted) (in 2D form);

FIG. 5 is the synthetic UV spectra of components 1 (solid), 2 (dashed), 3 (dotted), and 4 (dashdot);

FIG. 6 is the three-dimensional plot of the C1 data with interference free;

FIG. 7 is the five synthetic profiles of chromatogram C1 with noise and baseline drifting;

FIG. 8 is the plots of the coefficients (a) $C_6$, (b) $D_6^1$, (c) $D_6^2$, and (d) $D_6^3$ obtained by WT treatment on the five synthetic profiles as (FIG. 4) by wavelet Sym4 at scale 6;

FIG. 9 is the PCA plots of the results obtained by using CH2DC (a), WT2DC (b), and WT3DC (c) on treating the C1, C2 and C3 data sets generated with Fp=10.0%, Nl=0, and Bd=0 (See G1 of Table 3);

FIG. 10 is the PCA plots of the results obtained by using CH2DC (a), WT2DC (b), and WT3DC (c) on treating the C1, C2, and C3 data sets generated with Fp=6.0%, Nl=6.0%, and Bd=60% (See G4 of Table 3);

FIG. 11 is the pseudo-2D chromatogram of the three Chinese herbs, RA, RC, and RG with their intensities obtained by summing up absorbances at all the wavelengths measured at a given retention time;

FIG. 12 is the two-dimensional PCA plots of the three groups of herbs, RC (*), RG (+) and RA (o), by using results obtained from (a) CH2DC, (b) WT2DC, and (c) WT3DC; and FIG. 13 (a) is the three-dimensional PCA plots of the three groups of herbs, RC (*), RG (+) and RA (o), by using results obtained from WT3DC; and (b) the enlarged plot.

DETAILED DESCRIPTION OF PARTICULAR EMBODIMENTS

Reference will now be made in detail to an embodiment of the invention, examples of which are also provided in the following description. Exemplary embodiments of the invention are described in detail, although it will be apparent to those skilled in the relevant art that some features that are not particularly important to an understanding of the invention may not be shown for the sake of clarity.

Furthermore, it should be understood that the invention is not limited to the precise embodiments described below and that various changes and modifications thereof may be effected by one skilled in the art without departing from the spirit or scope of the invention.

In addition, improvements and modifications which may become apparent to persons of ordinary skill in the art after reading this disclosure, the drawings, and the appended claims are deemed within the spirit and scope of the present invention.

As shown in FIG. 1, one can find that the spectra, background and noise are signals in different morphological character. In other words, the noise, the signal and the drifting baseline are usually considered to be present in the contributions in high, medium, and low frequency band. Among them, spectral signals are relevant information and useful for later identification, while background and noise are regarded as interferences. Therefore, the WT according to the present invention is aimed at extracting useful signals of the raw data.

The basic idea of wavelet analysis is that of multiresolution. The concept of the multiresolution signal decomposition (MRSD) was introduced by Meyer and Mallat[12-13], and provides a powerful framework to understand wavelet decomposition. The goal of multiresolution is decomposition of a function space into a nested set of subspaces.

FIG. 2 shows the working scheme of the WT3DC procedure on processing the 3D chromatogram. With the predefined low-pass filter L and high-pass filter H (the output of L is referred to as the overall information while the output of H may be regarded as the detail information), the original signal $C_0$ at scale 0 is decomposed by the following expressions, $$C_j = L_r L_c C_{j-1} \quad (1)$$

$$D_j^1 = H_r L_c C_{j-1} \quad (2)$$

$$D_j^2 = L_r H_c C_{j-1} \quad (3)$$

$$D_j^3 = H_r H_c C_{j-1} \quad (4)$$

where the decomposition scale j is equal to 1, ..., J, with J being the maximal scale. $F_r G_c C_{j-1}$ represents the convolution of the $C_{j-1}$ matrix with filter G (H or L) by column (c) and then F (H or L) by row (r). The $C_j$ or $D_j$ matrix thus obtained is down-sampled by two after each convolution and is indicated as 2↓1 in FIG. 2.

Matrix $C_j$ is called the discrete approximation, and corresponds to the low frequency information, i.e., the smoother copy of the treated signal $C_{j-1}$. $D_j^1$, $D_j^2$, and $D_j^3$ are the discrete details of the signal. which contain information of vertical, horizontal, and vertical-horizontal high frequencies, respectively. The above algorithm, equations (1)-(4), can be repeated to decompose the discrete approximation successively from j=0 to the desired scale J to obtain the coefficients $C_j$ and $D_j$. Based on the property of the 3D chromatograms, either $C_j$ or $D_j^1$, $D_j^2$, and $D_j^3$ at a certain scale j can be utilized to construct the chromatographic fingerprint of the original signal for classification.

With the preprocessing power of WT using symlet wavelet, which is nearly symmetric and is a product of the well known Daubechies wavelets with modifications that increase the symmetry, while retain their relative simplicity, the interferences from noises and baseline drifting of the raw data can be minimized, and the data sizes can be significantly reduced. Meanwhile, the essential features of the new raw data still remain. Thus, the WT coefficients obtained are good for identification and they make pattern recognition of the samples to be conducted in a reliable, simple and easy way.

The flowchart shown in FIG. 3 shows how to use the WT3DC technique in practice. Firstly, the solid sample was grinded and extracted by the selected solvent to prepare the liquid sample. For liquid sample, further preparation may be needed. Secondly, the liquid samples are analyzed with HPLC-DAD (High performance liquid chromatography-diode array detector) and the three-dimensional chromatographic profiles are acquired. After data compression and decomposition by the WT treatment as shown in FIG. 2, the resulting coefficients can be utilized to perform model building, pattern recognition and classification in a more reliable and easier way.

To compare the performance of the proposed WT3DC method, a similar investigation was carried out by using the other methods, i.e., CH2DC and WT2DC, as pre-processing methods. In the CH2DC method, the 2D chromatogram was obtained by summing up the absorbance at all the wavelength channels. In the WT2DC method, the 2DC chromatograms obtained by the CH2DC method were treated with WT by using the same scale and wavelet as those used in the WT3DC method, and the discrete details were used for subsequent classification.

Generation of Simulated Synthetic Data for Testing WT3DC

Three types of artificial 3D chromatograms C1, C2 and C3 were synthesized and used in this particular example to test and evaluate the performance of the WT3DC method developed according to the present invention. FIG. 4 shows three (C1, C2 and C3) chromatograms representing three different kinds of samples of herbs or samples of the same herb from different sources. Each one consists of four components S1, S2, S3 and S4 with their corresponding peaks 1, 2, 3 and 4, with overlapping peaks 3 and 4 in a peak cluster. The peaks are well separated from one another. This kind of peak distribution is commonly found in chromatographic study of herbal medicine, a multi-component chemical system. Each of the four chromatographic peaks is of Gaussian shape (FIG. 5) and each component has its own ultraviolet (UV) spectrum containing two absorption peaks. In addition, interferences including variations of peak parameters, noise levels and baseline shifts were added to the C1, C2 and C3 chromatograms to assess the robustness of the method. In these three chromatograms, they all have the same number of components. In addition, the retention times of these components were the same. This was, of course, not the real situation for even samples of the same kind of herb collected from different sources or different seasons. Yet, if classification of these profiles performs well by using the WT3DC method, this should indicate that it will work in practical cases since these simulated systems are quite similar with real ones.

The four chromatographic peaks as shown in FIG. 4 were assumed to have the Gaussian shape and were generated by the following equation, $$f(t) = h_0 \exp\left[-4\ln(2)\left(\frac{t-t_0}{W_{1/2}}\right)^2\right] \quad (5)$$

where $h_0$, $t_0$ and $W_{1/2}$ are, respectively, the peak height, center position (retention time), and full-width-at-half-maximum (FWHM). They may or may not have the same values of the corresponding interference-free parameters $h_0'$, $t_0'$ and $W_{1/2}'$ (see Table 1) depending on whether the interferences were included or not. Also, the UV spectra of components 1, 2, 3, and 4 were simulated by using two Gaussian peaks (FIG. 5) with different peak heights, peak positions and FWHMs (Table 2) that are quite common for chemical components present in herbal medicine.

The 2D data set, M, of the 3D chromatograms C1, C2, or C3 were generated by $$M = \sum c_n s_n' \quad (2)$$
$$n = 1, 2, 3, 4$$

where $c_n$ and $s_n$ are, respectively, the chromatographic peak and the spectrum of the component n. FIG. 6 shows a plot of the 3D chromatogram of C1 with values of peak parameters given in the first rows of Tables 1 and 2.

TABLE 1

Values of the Gaussian peak parameters* used to generate chromatographic profiles C1, C2, and C3 (FIG. 5)

| Type | Peak | $t_0'$ | $W_{1/2}'$ | $h_0'$ |
|---|---|---|---|---|
| C1 | 1 | 3.0 | 1.0 | 1.0 |
|  | 2 | 7.0 | 1.2 | 0.5 |
|  | 3 | 12.0 | 1.3 | 0.7 |
|  | 4 | 14.0 | 1.5 | 1.4 |
| C2 | 1 | 3.0 | 1.0 | 1.0 |
|  | 2 | 7.0 | 1.2 | 0.8 |
|  | 3 | 12.0 | 1.3 | 0.5 |
|  | 4 | 14.0 | 1.5 | 1.0 |
| C3 | 1 | 3.0 | 1.0 | 1.2 |
|  | 2 | 7.0 | 1.2 | 0.6 |
|  | 3 | 12.0 | 1.3 | 1.0 |
|  | 4 | 14.0 | 1.5 | 1.4 |

*see text for the definitions of the parameters.

TABLE 2

Values of the Gaussian peak parameters* used to generate the UV spectra of components S1, S2, S3, and S4 (FIG. 6)

| Components | Peak | $t_0'$ | $W_{1/2}'$ | $h_0'$ |
|---|---|---|---|---|
| S1 | 1 | 20 | 8.9 | 1.0 |
|  | 2 | 60 | 22.4 | 0.3 |
| S2 | 1 | 25 | 13.4 | 0.5 |
|  | 2 | 65 | 26.8 | 0.8 |
| S3 | 1 | 35 | 17.9 | 1.0 |
|  | 2 | 70 | 33.5 | 0.6 |
| S4 | 1 | 15 | 8.9 | 1.2 |
|  | 2 | 50 | 22.4 | 0.8 |

*see text for the definitions of the parameters.

Table 1 lists the values of the Gaussian parameters of the four component peaks used to generate the three types of 3D chromatograms C1, C2 and C3. It can be seen that they have the same $t_0'$ and $W_{1/2}'$ values but different $h_0'$ values. In chromatographic study, this means that all the chemical components are the same in the three systems C1, C2 and C3 but differ in concentrations. In each type of chromatogram, 30 data sets were generated by adding interferences to C1, C2, or C3 to certain extent in the following way. Three common kinds of interferences, fluctuation of the peak parameter (Fp), baseline drifting (Bd), and noise level (Nl) were investigated in this work (see Table 3). The fluctuation of the peak parameters including peak height, retention time, and FWHM, was adjusted by a single variable (Fp). The following formulas were used to calculate the parameters $h_0$, $t_0$ and $W_{1/2}$ with interferences included in each peak to give the simulated chromatographic profile, $$t_0 = (1+Fp*rand)t_0' \quad (3)$$

$$W_{1/2} = (1+Fp*rand)W_{1/2}' \quad (4)$$

$$h_0 = (1+Fp*rand)h_0' \quad (5)$$

where rand represents random number with value between 0 and 1. In chromatographic study, this means that the peak heights, retention times, and FWHMs of all chemical components are influenced. This could be the effect of small temperature changes between the chromatographic runs, differences in the pressure or slow ageing of the chromatography column. 30 random numbers were used for equations (3)-(5) to include interference into the peak parameters in C1, C2 or C3. This leads to 30 different synthetic data sets for treatment. In creating a chromatogram, the peak ($c_n$) was generated by using equation (1) with peak parameters for C1, C2 or C3 as given in Table 1. As for the baseline drifting, it was simulated by using the second order of polynomial while the noise with normal random distribution was added to C, before it was utilized to construct the 2D data set via equation (2). The peak height of $c_n$ was employed to produce both the baseline drifting and noise level. For each Fp value (see data discussion), 30 data sets of corresponding $h_0$, $t_0$ and $W_{1/2}$ were generated via equations (3)-(5) by using 30 random numbers. These may mean samples of a certain herb being collected from different sources or in different seasons.

The effect of the variations of the interference parameters of Fp, Nl and Bd on the classification result was investigated by four different groups, namely as G1, G2, G3 and G4 (Table 3). In G1, G2, G3, two of these three parameters were set assigned to have zero value to investigate how good the methods performance on variation of the remaining interference parameter (Table 3). For example, in G1 only the effect of Fp was investigated with Nl and Bd being set to have zero value. As for G4, the variations of all the three parameters were considered together.

As mentioned above, the only difference between a peak with the corresponding peaks in chromatograms C1, C2 and C3 (Table 1) is the peak height, i.e., the concentration of the components concerned. Since the C1, C2 and C3 chromatograms of, say, the related samples are very similar to one another, classification based on these chromatographic data is expected to perform poorly. Again, if the proposed method works well, then it should work even better in the real situation.

Real World HPLC-DAD HM Data for Testing WT3DC

Instruments: Hewlett Packard 1100 Series HPLC Pump and Hewlett Packard 1100 series Photodiode Array Detector (DAD)

Materials: Three popular HMs, namely Radix angelicae sinensis (RA), Rhizoma Ligustici chuanxiong (RC), and Cortex cinnamomi (RG) were collected from different geographic sources with sample size of 84, 99 and 93 respectively to test the performance of WT3DC.

Extraction: 0.5 g powder of each sample was extracted with 30 ml methanol, and then homogenizer was used to beat up the mixture for two minutes at a rate of 11000 rpm. After filtering off the residue, methanol was evaporated away by using a rotary evaporator. The remaining residue was dissolved in 5 ml of methanol. The sample solution was passed through a SEP-PAK $C_{18}$ cartridge (Waters Assoc., U.S.A.) before injection.

Separation: A $C_{18}$ reversed-phase HPLCcolumn (Lichrosorb RP-18, 5 micron, 4.6 mm×200 mm) was used. Mobile phase used for the HPLC is methanol: buffer=10:90 (0-60 min.) and 100:0 (after 60 min.), where the buffer is a mixture $KH_2PO_4$ and $H_3PO_4$ with pH=3. Flow Rate of the HPLC runs is set at 0.7 ml/min and UV absorptions are recorded from 210 to 400 nm.

Data Analysis

All data analysis was performed on a Pentium 4 personal computer. All programs for calculation were in-house programs in MATLAB® 6.5 (The Mathworks, Natick, Mass.) for windows.

Preprocessing 2D Chromatographic Data Set with WT3DC and Selection of Coefficients As shown in FIG. 6, WT treatment produced good results in improving the quality of the smooth chromatograms and in reducing its data size with minimal loss of information. The common WT procedure used includes different steps of signal decomposition, selection of wavelet coefficients after WT treatment, and the reconstruction of the original signal from the retained coefficients. In this particular embodiment, the coefficients obtained from symlet 4 WT treatment (symlet 4 WT treatment is a well known method to people skill in the this filed, who can perform the symlet 4 treatment on the given data without difficult) with no signal reconstruction were directly used for classification. Four types of wavelet coefficients $C_j$, $D_j^1$, $D_j^2$ or $D_j^3$ at scale j are generated from WT3DC treatment by Matlab, a well-known mathematical scripting language. Here $C_j$ represents the approximation coefficients, while $D_j^1$ and $D_j^2$ denote the horizontal and vertical detail coefficients respectively. As for $D_j^3$, it represents the diagonal detail coefficients. To investigate which type is good for this study, we used the last set of interference parameters of G4 with the degree of baseline drifting being 60%, the noise level 6.0%, and Fp having values of 4%, 6% and 8% respectively (The bottom row in Table 3). FIG. 7 shows the plots of the five pseudo-2D chromatograms of C1 thus obtained. It is obvious that the profile is highly variant owing to the noise and the baseline drifting as expected. These five data sets were transformed with wavelet Symmlets No. 4 (Sym4 or symlet 4) at scale 6. FIG. 8 depicts the WT coefficients that obtained from FIG. 6 with plots (a), (b), (c), and (d) corresponding to the coefficients $C_6$, $D_6^1$, $D_6^2$, and $D_6^3$. It can be seen that the noise has been eliminated in all these coefficients (FIG. 8) as compared to the original plots (FIG. 7). The five plots of the coefficients $C_6$ (FIG. 8(a)) and $D_6$ (FIG. 8(c)) are still different from one another, while the deviations between the five plots of $D_6^1$ (FIG. 8(b)) and $D_6^3$ (FIG. 8(d)) nearly converts to a single line with much less variation. The main reason is that the former two quantities still contain the baseline information. As for the later two, the baseline drifting have been removed as the fluctuation are small (FIG. 8) but the matrix $D_6$ keeps more detail information compared with $D_6^1$. This may be due to that $D_6$ gives balanced chromatographic and spectral information of the original signal while $D_6^1$ contains more spectral and $D_6^2$ more chromatographic information, correspondingly. Therefore $D_6^3$ was used for subsequent investigation.

It was reported that the vanishing moment of the wavelet is an important factor for eliminating the fluctuating background. Similarly, the effect of the baseline drifting can also be removed with the proper selection of vanishing moment. Wavelets with different vanishing moments adopted in the transform may give different results. It was found in the present invention that the Sym4 wavelet with a vanishing moment of 4 is good enough for the removal of most baseline drifting. Therefore, in the following discussion on the WT treatment, only results obtained by Sym4 with a vanishing moment of 4 are used. The optimal scale level to be utilized in WT treatment depends largely on the data size and the noise level and is mainly selected based on the classification accuracy achieved though it can be estimated by visual inspection of the quality of classification of the Principal Component Analysis (PCA) plot. The relationship between the first two principal components (PC1-PC2) is utilized in all PCA plots in the following discussion. PCA is a very popular method in applied statistical work and data analysis, and it has a good ability to summarize multivariate variation. Although symlet4 was a preferred wavelet used in this example, other wavelet, such as, for example, daubechies wavelet, or ceyer wavlet also provide satisfactory results.

Performance of WT3DC on Synthetic Chromatographic Data Sets

In order to investigate the performance of the proposed WT3DC method, 2D data sets with different noise levels, baseline drifts, and fluctuating of peak parameters ($h_0$, $t_0$ and $W_{1/2}$) were simulated as described previously. They were all transformed with Sym4, and the coefficients $D_6^3$ were utilized for the classification. The commonly used PCA method was utilized to classify the three types of chromatograms C1, C2, and C3, and the classification accuracy was estimated based on Euclidean distance ($D_E$) and Manhattan City Block distance ($D_M$). For comparison, the same PCA classification procedure was applied using results from methods CH2DC and WT2DC using the pseudo-2D chromatogram. The coefficients obtained with the same scale (J=6) and wavelet (Sym4) as used in the WT3DC transform was employed in WT2DC.

TABLE 3

Classification accuracy (%) of all the synthetic C1, C2 and C3 data sets as obtained by the three methods CH1D, WT1D and WT3DC.

| Value of Parameters | CH1D | | WT1D | | WT3DC | |
|---|---|---|---|---|---|---|
| | $D_E$ | $D_M$ | $D_E$ | $D_M$ | $D_E$ | $D_M$ |
| G1 Nl = 0, Bd = 0 | | | | | | |
| Fp = 5.0% | 100.0 | 100.0 | 100.0 | 100.0 | 100.0 | 100.0 |
| Fp = 10.0% | 95.6 | 95.6 | 95.6 | 95.6 | 100.0 | 97.8 |
| Fp = 15.0% | 76.7 | 71.1 | 83.3 | 83.3 | 87.8 | 91.1 |
| G2 Bd = 0, Fp = 0 | | | | | | |
| Nl = 5.0% | 100.0 | 100.0 | 100.0 | 100.0 | 100.0 | 100.0 |
| Nl = 10.0% | 100.0 | 100.0 | 100.0 | 100.0 | 100.0 | 100.0 |
| Nl = 15.0% | 100.0 | 100.0 | 100.0 | 100.0 | 100.0 | 100.0 |
| G3 Nl = 10, Fp = 0 | | | | | | |
| Bd = 50% | 88.9 | 88.9 | 100.0 | 100.0 | 100.0 | 100.0 |
| Bd = 100% | 64.4 | 60.0 | 100.0 | 100.0 | 100.0 | 100.0 |
| Bd = 150% | 53.3 | 51.1 | 100.0 | 100.0 | 100.0 | 96.7 |
| G4 Nl = 6.0%, Bd = 60% | | | | | | |
| Fp = 2.0% | 84.4 | 83.3 | 84.4 | 83.3 | 100.0 | 100.0 |
| Fp = 4.0% | 83.3 | 80.0 | 83.3 | 72.2 | 100.0 | 98.9 |
| Fp = 6.0% | 83.3 | 76.7 | 83.3 | 71.1 | 100.0 | 97.8 |
| Fp = 8.0% | 80.0 | 71.1 | 78.9 | 68.9 | 98.9 | 97.8 |

Remark:
Fp, Ne and Pd denote the fluctuation of the peak parameters, the noise level, and the degree of baseline drifting, respectively, while $D_E$ and $D_M$ represents the Euclidean distance, denotes the Manhattan distance, respectively.

Table 3 lists the classification results obtained from the three different methods of CH2DC, WT2DC, and WT3DC upon variation of all the parameters Fp, Nl and Bd. It is interesting to note that all three methods are quite free from noise level and give good classification accuracy (see G2 in Table 3). As for the other interference groups, the overall performance of WT3DC is better than WT2DC and CH2DC in general. With regard to the variation in peak parameters, the three methods perform perfectly with Fp=5.0%. Yet, the performance deteriorates with higher Fp values. As for the effect of baseline drifting both WT3DC and WT2DC are quite free from the change even with Bd up to 150% (see G3 in Table 3). However, CH2DC perform progressively poorer with increase in Bd as larger Bd reduces the signal to noise ratio leading to the difference between the samples being concealed. From the results obtained from G1, G2, and G3 (Table 3), it can be concluded that all these methods are more sensitive to the change in peak parameters. With variations in Nl, Bd and Fp, the classification accuracy of WT3DC is still very high with values close to 100% compared to those of CH2DC and WT2DC. From data treatment point of view, WT3DC minimizes both the noise level and baseline drift. The same is true for WT2DC, but not for CH2DC. Yet, the WT3DC has an advantage in retaining balanced information from both chromatograms and spectra, while the other two methods keep more chromatographic information. This makes WT3DC outperform the other two methods.

To give a better illustration on the performance of the three methods, the PCA classification results obtained under two different conditions were plotted and shown in FIG. 10 (G4 group) and FIG. 9 (G1 group). It is worthwhile to note that the chromatograms belonging to the same types of chromatograms C1, C2 or C3 can be separated into different clusters using WT3DC in both plots. There is clear that its classification performance is superior to the others. The reason is that on top of removal of noise and baseline drifting, the WT3DC method keeps more information of the spectra. Therefore it is more stable with respect to the variation of the interference parameters used here for validation.

Performance of WT3DC on Real World HPLC-DAD Data Sets

In order to scrutinize the applicability of the proposed WT3DC method in real cases, it was applied to classify 276 herbal medicine (HM) sample, named Radix angelicae sinensis (RA), Rhizoma Ligustici chuanxiong (RC), and Cortex cinnamomi (RG) from different geographic locations. FIG. 11 shows the 2D HPLC-DAD chromatograms of individual samples of the three herbs as obtained by the summing up the absorbance of all wavelengths at a given retention time in the 3D chromatograms. It is expected that the chromatograms of RA and RC are very similar to each other because both contain the major components ligustilide and butylidenephthalide at the retention time 48.3 min. and 46.2 min, respectively. Following the WT3DC procedure, data sets of all the samples were transformed by using Sym4 up to scale 5. It was found that scale 5 was good enough to get the desired classification accuracy and hence results obtained from scale 5 instead of 6 being used for the synthetic data. The classification results obtained with CH2DC and WT2DC methods are also presented here for comparison. The $D_5^3$ and $D_5$ obtained by WT3DC and WT2DC methods were used for subsequent analysis and discussion.

FIG. 12 gives the PCA plots by using the results obtained from the above three methods. It can be seen in the plot that the treated data obtained by the CH2DC method failed to classify the herbal samples into three distinct groups. Owing to the effect of the baseline drifting, the Rhizoma Ligustici chuanxiong (RC) samples cannot be distinguished from the Radix angelicae sinensis (RA). In addition, due to the variation of the sample sources and the similarity of the chromatographic profiles, the data points from the RA and RC groups are highly dispersed and partly overlapped. With the correction of the baseline drifting, the WT2DC method provides a better classification result. The RC samples are clustered into a single region and separated from the RA group. However, the performance on RA and RC is still not satisfactory because it is sensitive to the variation of other parameters, such as retention time, peak height, and others.

The WT3DC method, on the other hand, performed significantly better than both CH2DC and WT2DC in classification of the three herbal samples, though there was still certain degree of dispersion (see Table 3). All the three groups RA, RC and RG were almost completely separated as shown in FIG. 13. FIG. 13(a) shows the three-dimensional PCA plots of the three groups of herbs by using the WT3DC results and FIG. 13(b) shows an enlarged region in FIG. 13(a). The three-dimensional PCA plots give us a clearer picture on how well samples of the three herbs are separated. In addition, the distances within the same groups are smaller than those obtained with CH2DC or WT2DC. (Table 3). The classification accuracy was also calculated using the same procedure as that used for the simulated data set. The WT3DC method gave an accuracy of 98.55% (4 wrong answers out of total 276 sample numbers), and is better than 92.03% (22 wrong) and 92.75% (20 wrong) as obtained from methods CH2DC and WT2DC, respectively.

Limitation of WT3DC

The WT3DC according to the present invention is useful for pre-processing smooth 3D data set, including, but not limited to, HPLC-DAD chromatograms, and it should not be applied to non-smooth data sets, such as bar-like mass spectral data sets, for example, GC-MS (Gas chromatography Mass spectrometry). With non-smooth data sets, the results obtained would be misleading.

Chromatographic fingerprint has been proven to be an effective technique for studying complex chemical samples such as herbal medicine. The conventional signal processing methods are based on 2D chromatogram and hence usually sensitive to the variation of the experimental detection and do not make use of chemical information from chromatograms. Aim at improving these methods, the WT3DC of the present invention achieves good results. With the preprocessing power of WT, the interferences from noise and baseline drifting of the raw data are eliminated, and also the data size is significantly reduced. Thus, the WT coefficients obtained are good for classification and identification. As demonstrated by the results of the simulated data in this work, retaining both chromatographic and spectral information gives the proposed WT3DC method an obvious advantage over those 2D methods. The WT3DC method was found to be more robust with respect to the interferences originating from noise level, baseline drifting, and the peak parameters that are commonly encountered in chromatographic and other studies. The WT3DC method was also successfully applied to classify three groups of HM with higher accuracy, compared with the existing method based on 2D chromatogram with and without WT pretreatment. In addition, as it is apparent to people with ordinary skill in the art, the above exemplified method may be modified and applied to classify other types of smooth data set, for example, those from CE-DAD, HPLC-IR, GC-IR, etc.

REFERENCES

[1] WHO, General Guidelines for Methodologies on Research and Evaluation of Traditional Medicines, 2000, p. 1.
[2] SFDA, Chinese Traditional Patent Medicine vol. 22 (2000), pp. 671-675 (in Chinese).
[3] Y. Z. Liang, P. S. Xie, K. Chan, J. Chromatogr. B. 812 (2004) 53.
[4] D. K. W. Mok, F. T. Chau Chemical information of Chinese medicines: A challenge to chemist, Chemo. Intelli. Lab. Syst. in press.
[5] J. O. Ramsay, C. J. Dalzell, J. R. Statist. Soc. B., 1991, 53, 233.
[6] J. O. Ramsay, B. W. Silverman, Functional data analysis, $2^{nd}$, Springer, N.Y. (2005)
[7] C. J. Xu, Y. Z. Liang, Y. Li, Y. P. Du Analyst, 128 (2003) 75-81.
[8] F. T. Chau, Y. Z. Liang, J. Gao, X. G. Shao, Chemometrics: From Basics to Wavelet Transform, John Wiley and Sons, Hoboken (2004).
[9] B. Walczak, D. L. Massart. Trends in Anal. Chem. 16 (1997)451
[10] X. G. Shao, A. K. M. Leung, F. T. Chau, Accouts. Chem. Res. 36 (2003) 276
[11] K. Jetter, U. Depczynski, K. Molt, A. Niemöller, Principles and Applications of Wavelet Transformation of Chemometrics. Anal. Chim. Acta. 420 (2000) 169.
[12] Y. Meyer, Ondelettes et operateurs, Tome 1, Ondelettes. Herrmann, Paris, 1990.
[13] S. Mallet, IEEE Trans. Pattern Anal. Mach. Intell. 11 (1989) 674-693.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

We claim:

1. A method of identifying or authenticating a substance containing a plurality of chemical ingredients, the method comprising:
    a. obtaining a data set from a sample of a substance using a measuring instrument;
    b. transforming said data set using a wavelet with a vanishing moment to obtain a set of coefficients at a decomposition scale; and c. Optionally classifying said set of coefficients with a classification method to generate a classification result; wherein said data set is a 3D chromatogram of intensity versus wavelength versus retention time, and said substance is an herbal medicine or an agricultural plant.

2. The method of claim 1, wherein steps (a) to (c) are performed on at least two substances whose identity is known or unknown.

3. The method of claim 1, wherein said data set is a smooth data set.

4. The method of claim 1, wherein said substance contains a plurality of chemical compounds.

5. The method of claim 1, wherein said wavelet is Symlet4.

6. The method of claim 5, wherein said vanishing moment is 4.

7. The method of claim 6, wherein said set of coefficients is at a decomposition scale of 5 or 6.

8. The method of claim 7, wherein said classification method is a Principal Component Analysis (PCA) method.

9. The method of claim 3, wherein said smooth data set is obtained from an instrument of CE-DAD, HPLC-IR, HPLC-DAD or GC-IR.

10. The method of claim 2, wherein at least one of said substances is of known identity and at least one of said substances is of unknown identity.

11. The method claim 10, further comprising comparing said classification result of said substance of known identity and of said substance of unknown identity.

12. A device for identifying or authenticating a substance containing a plurality of chemical ingredients, comprising:
   a. a data interface to connect with a measuring instrument and to receive a data set from said measuring instruments wherein said data set is a 3D chromatogram of intensity versus wavelength versus retention time of a sample of a substance; and
   b. a data compression module capable of performing a wavelet transform on said data set to produce a set of coefficients at a given decomposition scale, said module allowing selection of a wavelet, a vanishing moment, and a decomposition scale for performing said wavelet transform; wherein said substance is an herbal medicine or an agricultural plant.

13. The device of claim 12, further comprising a data classification module for performing classification on said set of coefficients and outputting a classification result.

14. The device of claim 13, wherein said data compression module is implemented in hardware, software or combination of hardware and software.

15. The device of claim 14, wherein said data classification module is implemented in hardware, software or combination of hardware and software.

16. The device of claim 15, wherein said device is a personal computer,
   said data interface is a serial port, parallel port, firewire port, USB port, WiFi connection, Bluetooth connection or infrared connection, and
   said data compression module and data classification module are implemented in software.

17. The device of claim 13, wherein said classification result is visually presented on a screen or as a printout on paper.

18. The device of claim 12, wherein said measuring instrument is selected from the group consisting of CE-DAD, HPLC-IR, HPLC-DAD and GC-IR.

* * * * *